United States Patent [19]

Fauss et al.

[11] Patent Number: 4,791,229
[45] Date of Patent: Dec. 13, 1988

[54] PREPARATION OF ARYL CYANAMIDES FROM ARYLAMINES AND CYANOGEN CHLORIDE

[75] Inventors: Rudolf Fauss, Cologne; Hans-Jochem Riebel, Wuppertal, both of Fed. Rep. of Germany

[73] Assignee: Bayer Aktiengesellschaft, Leverkusen, Fed. Rep. of Germany

[21] Appl. No.: 922,635

[22] Filed: Oct. 24, 1986

[30] Foreign Application Priority Data

Oct. 26, 1985 [DE] Fed. Rep. of Germany ....... 3538128

[51] Int. Cl.⁴ ................. C07C 125/08; C07C 147/12; C07D 307/91
[52] U.S. Cl. ..................................... 564/105; 564/103
[58] Field of Search ............................... 564/103, 105

[56] References Cited

U.S. PATENT DOCUMENTS

| | | | |
|---|---|---|---|
| 2,194,075 | 3/1940 | Roblin | 564/103 |
| 2,194,076 | 3/1940 | Roblin | 564/103 |
| 2,194,077 | 3/1940 | Roblin | 564/103 |
| 3,830,928 | 8/1974 | Mrozik | 564/103 X |

FOREIGN PATENT DOCUMENTS

| | | | |
|---|---|---|---|
| 2019214 | 10/1970 | Fed. Rep. of Germany | 564/103 |
| 2334821 | 1/1974 | Fed. Rep. of Germany | 564/103 |
| 2433939 | 2/1976 | Fed. Rep. of Germany | 564/103 |

OTHER PUBLICATIONS

Ferri: Reaktionen der organischem Synthese ("Reactions of Organic Synthesis"); p. 668 (1978).
Houben-Weyl: Methoden der organischen Chemie ("Methods of Organic Chemistry"), vol. E 4, pp. 981/82 and 988/89.
V. Migrdichian: The Chemistry of Organic Cyanogen Compounds, p. 102 et seq. (1947).
M. P. Pierron (Ann. chim. phys. [8] 15, pp. 145–181 (1908).
Synthesis 1976, pp. 591–593 (Cockerill et al.).
J. Chem. Soc., Perkin Trans. I 1984, pp. 147–153 (Birkinshaw et al.).
Journal of the Indian Institute of Science, Section A, Bangalore, 29 A, p. 5 (1946).
Itaya and Ogawa (Tetrahedron 38, 176 (1982)).
J. Praktische Chemie 317 (1975) 6, pp. 907–918 Bacaloglu et al. I).
J. Chem. Soc., Perkin Trans. II 1976, 5, pp. 524–531 (Bacaloglu et al.

*Primary Examiner*—Floyd D. Higel
*Attorney, Agent, or Firm*—Sprung Horn Kramer & Woods

[57] ABSTRACT

A process for the preparation of an aryl cyanamide comprising reacting an arylamine of the formula

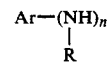

in which
Ar is aryl,
R is hydrogen or alkyl, and
n is 1, 2 or 3, (excepting 2-nitroaniline, 4-nitroaniline and arylamines having a nucleophilic character equal to or lower than 2-nitroaniline and 4-nitroaniline), with cyanogen chloride in 1–2 times the molar amount per mole of amino group of the arylamine initially in a homogeneous liquid phase using as reaction medium acetic acid (which is optionally diluted with water and/or a water-miscible, organic auxiliary solvent) in the presence of 1–1.5 molar equivalents of an auxiliary base for each amino group of the arylamine, there being more cyanogen chloride than equivalents of auxiliary base present in the reaction mixture at any point in time of the reaction, the pH of the reaction mixture being maintained below 7.

10 Claims, No Drawings

PREPARATION OF ARYL CYANAMIDES FROM ARYLAMINES AND CYANOGEN CHLORIDE

The invention relates to a new, widely applicable process for the preparation of aryl cyanamides by reacting the corresponding arylamines with cyanogen chloride, which makes it possible for the first time to convert even weakly basic arylamines into the desired cyanamides in a high state of purity and in very good yields by this route. The aromatic cyanamides are valuable intermediate products in various fields of organic chemistry.

According to the general review literature amines can be reacted with cyanogen halides to give cyanamides (Ferry: Reaktionen der organischen Synthese ("Reactions of organic synthesis"); page 668 (1978); Houben-Weyl: Methoden der organischen Chemie ("Methods of organic chemistry"), volume E 4, pages 981/82 and 988/89; and V. Migrdichian: The Chemistry of Organic Cyanogen Compounds, page 102 et seq. (1947)).

If the original literature is studied precisely, however, it is rapidly discovered that no examples with information on satisfactory yields and purity of the corresponding cyanamides are available for reactions of cyanogen halides with weakly nucleophilic or weakly basic aromatic amines; although fairly strongly nucleophilic or basic amines in most cases give satisfactory to good yields, in these cases the products are impure and an involved purification stage is required.

Within the scope of the present invention weakly nucleophilic aromatic amines constitute amines having a weaker nucleophilic character than unsubstituted aniline. In default of a generally accepted, usable parameter for nucleophilic character, the basicity is taken as an approximate criterion—as is customary in the literature.

The most systematic article relating to the reaction of cyanogen halides with amines, which also includes the weakly basic aromatic amines within the scope of the present invention, is that by M. P. Pierron (Ann. chim. phys. [8] 15, pages 145–181 (1908)).

As Pierron states on pages 157 et seq. of this publication, he is successful in reacting aromatic amines with cyanogen bromide in an aqueous or aqueous alcoholic suspension or solution in the presence of an alkali metal bicarbonate. Pierron uses cyanogen bromide, since this—in addition to being easy to handle in the laboratory—is hydrolyzed less rapidly in the presence of water and/or alkali than cyanogen chloride, which is of industrial importance (page 158 above). Additionally, higher reaction temperatures can be reached with cyanogen bromide by virtue of its boiling point.

According to the tests carried out by the applicant, however, the yields are estimated too high by Pierron and/or the purity of the resulting cyanamides is inadequate. For example, Pierron obtains the corresponding 3-nitrophenyl cyanamide from 3-nitroaniline in a crude yield of 76% of theory.

These figures were already reduced in the researches described in U.S. Pat. No. 3,830,928 and German patent specification No. A 2,334,821. The authors found it necessary to purify the crude product—prepared by a method modelled on the instructions given by Pierron—and then achieved a yield of pure substance (3-nitrophenyl cyanamide) of only 41% of theory.

According to the investigations carried out by the applicant, it is not possible to react weakly basic amines with cyanogen chloride to give the corresponding cyanamides in a satisfactory yield and purity by the procedure of Pierron.

Similarly, the other processes, otherwise customary, for the preparation of cyanamides (literature: Synthesis 1976, page 591; and J. Chem. Soc., Perkin Trans. I 1984, pages 147 et seq.) are not applicable to the reaction of weakly basic amines. According to investigations carried out by the applicant, this results either in no reaction or in the side reactions already described by Pierron, for example saponification of the cyanogen chloride in the alkaline medium or further reaction of the cyanamides with as yet unreacted amine to give guanidines or polymeric secondary products. At best, very low yields are achieved.

For example, if the synthesis of 4-chlorophenyl cyanamide described in Journal of the Indian Institute of Science, Section A, Bangalore, 29 A, page 5 (1946)—a reaction analogous to Pierron's process—is repeated, hardly any product is obtained, if the reaction is carried out with cyanogen chloride.

Itaya and Ogawa (Tetrahedron 38, 176 (1982)) describe the reaction of certain alkylaminoimidazoles with cyanogen bromide in an acetic acid/sodium acetate buffer to give the corresponding cyanamides. The authors use a large excess (5-molar) of cyanogen bromide, operate in a suspension during the entire reaction and only obtain yields between 25 and 56% of theory.

This variant of synthesis is not suitable for an industrial process, however. Cyanogen bromide is unsuitable for industrial reactions by virtue of its physical properties (boiling point: 62° C.; melting point: 50° C.) and its instability on storage (Organic Synthesis, Coll. Vol. II, page 151, note 4). In addition, the use of such large amounts, exceeding the stoichiometric equivalent, of a chemical of such toxicity entails considerable problems of working up and safety.

If the process of Itaya and Ogawa is carried out with cyanogen chloride instead of cyanogen bromide, if the excess of cyanogen halide is reduced, for example to a twice molar amount, and if the reaction is carried out with weakly basic amines, only impure cyanamides are obtained and in an unsatisfactory yield.

The side reaction of guanidine formation or urea formation becomes particularly prominent when more strongly nucleophilic or basic aromatic amines are reacted. Bacaloglu and collaborators (j. Praktische Chemie 317 (1975) 6, pages 907–18; and J. Chem. Soc., Perkin Trans. II 1976, 5, pages 524–31) have investigated this and have been able to explain it in a reasonable manner.

DE-A 2,019,214 describes a process for the preparation of biscyanamides of strongly basic amines. Different variants of the cyanogen chloride/amine reaction are described here in detail in Examples 2–10. Although the yields of crude product are consistently satisfactory to good, the cyanamide content of the crude products is only up to 90%. The biscyanamides are mainly employed in the polymer field, and here cyanamide contents of a maximum of 90%, as described, are not adequate. In order to obtain the desired cyanamides in a sufficiently pure form, it is necessary to pass through a high-loss purification stage; there is no indication of the yield of pure substance.

Accordingly, there was an urgent technical need for a generally applicable process for the preparation of cyanamides of aromatic amines, including weakly basic amines, which makes it possible to employ cyanogen chloride and, at as low an excess of the latter as possible, gives a high yield of product in a high state of purity.

It has now been found that aryl cyanamides are obtained in high yields and in a high state of purity by reacting arylamines of the general formula I

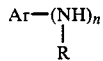

wherein

Ar represents aryl which is optionally additionally substituted,

R represents hydrogen or alkyl and n denotes the numbers 1, 2 or 3, (excepting from these, however, 2-nitroaniline and 4-nitroaniline and arylamines having a nucleophilic character as low as, or even lower than, 2-nitroaniline and 4-nitroaniline), with cyanogen chloride (Cl-CN), if the reaction is initially carried out in a homogeneous liquid phase using acetic acid (which is optionally diluted with water and/or a water-miscible, organic auxiliary solvent) as the reaction medium, and if 1–2 moles of cyanogen chloride and 1–1.5 molar equivalents of an auxiliary base are employed for each amino group, per mole of arylamine (I), there being more cyanogen chloride than equivalents of auxiliary base added to the reaction mixture at any point in time of the reaction, so that the pH of the reaction mixture remains below 7.

The arylcyanamides which can be prepared by the process according to the invention can be described by means of the general formula (II)

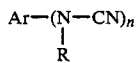

wherein Ar, R and n have the meanings indicated above in formula (I), and thus also embrace the cyanamides of weakly basic arylamines, excepting only cyanamides of the arylamines designated under formula (I) in which the nucleophilic character is too weak.

In the light of the state of the art set forth above, it must be described as very surprising that it is possible, under the conditions of the process according to the invention, to convert aromatic amines—including weakly basic arylamines—into the corresponding aryl cyanamides in high yields and at the same time in a state of high purity. In this respect, the broad applicability of the new process is a particular advantage; the reaction only fails to work with arylamines which are too weakly nucleophilic. Thus, for example, it is still possible for 3-nitroaniline to react readily, whereas 2-nitroaniline and 4-nitroaniline no longer react with cyanogen chloride.

If 3-fluoroaniline is used as the starting material, the process according to the invention can be represented by the following equation:

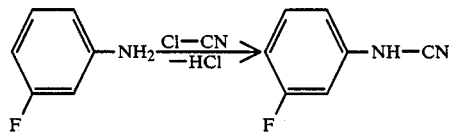

The arylamines which can be used as starting materials are defined in general by the formula (I). Preferred arylamines are those of the formula (I) wherein Ar represents phenyl, 1-naphthyl or 2-naphthyl, it being possible for these radicals to be optionally monosubstituted or polysubstituted by identical or different substituents, preferably by the following substituents: fluorine, chlorine, bromine, iodine, ($C_1$–$C_4$)-alkyl (in particular methyl and ethyl), ($C_1$–$C_4$)-alkoxy (in particular methoxy and ethoxy), ($C_1$–$C_4$)-alkylthio (in particular methylthio), ($C_1$–$C_2$)-alkylsulphonyl (in particular methylsulphonyl), trifluoromethyl, trifluoromethoxy, trifluoromethylthio, nitro, ($C_1$–$C_4$)-alkoxycarbonyl (in particular methoxycarbonyl and ethoxycarbonyl), aminocarbonyl, ($C_1$–$C_4$)-alkylaminocarbonyl and di-($C_1$–$C_4$)-alkylaminocarbonyl, phenylaminocarbonyl (which is optionally substituted in the phenyl ring, for example by halogen, lower alkyl or nitro), ($C_1$–$C_4$)-acylamino (for example acetylamino), di-($C_1$–$C_4$)-alkylamino (for example dimethylamino), aminobenzyl, aminophenoxy or aminophenylsulphonyl; it also being possible for the aryl radicals mentioned to be substituted by fused (preferably 5-membered) heterocyclic rings; and wherein further R preferably represents hydrogen or ($C_1$–$C_4$)-alkyl (in particular methyl and ethyl) and n preferably represents 1 and 2.

Arylamines which are particularly preferred as starting materials are those of the general formula (I) in which the nucleophilic character (or basicity) is weaker than that of unsubstituted aniline.

The following arylamines may be mentioned as particular examples, which are also embraced by the general formula (I), of starting compounds:

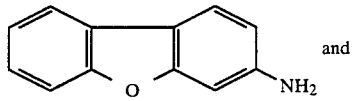

and

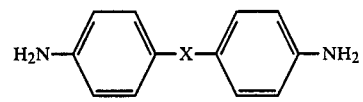

wherein X can represent —$CH_2$—, —O— or —$SO_2$—.

The following compounds may be mentioned as typical examples of aromatic diamines of the general formula (I) in which n=2:

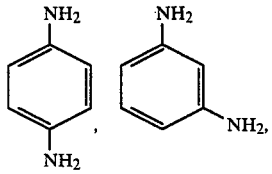

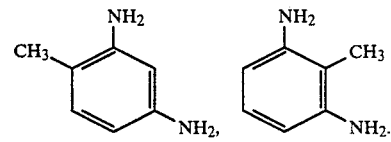

In principle it is possible to employ as starting materials any aromatic amines (mono-, di-, and tri-amines) which have a stronger nucleophilic character than 2-nitroaniline or 4-nitroaniline and in which further substituents are inert towards cyanogen chloride, provided that these amines—for example in the form of their acetates—are soluble in the acetic acid reaction medium used.

The limit indicated arises from the simple fact that arylamines of too weak a nucleophilic character no longer react with cyanogen chloride in the process according to the invention. Whether an arylamine is still suitable as a starting material for the process according to the invention can be determined without difficulty by means of a simple preliminary test.

It is, of course, also possible to employ cyanogen bromide instead of cyanogen chloride in the process according to the invention, but this brings no advantages.

In order to achieve high yields of pure products it is necessary to carry out the reaction of the aromatic amines with cyanogen chloride in its initial phase in a homogeneous, liquid phase. If the starting amine is not completely dissolved at the commencement of the reaction, in the case of some amines part of the amount of amine is not reacted and end products containing corresponding impurities are obtained.

It is preferable to carry out the reaction in dilute acetic acid as the reaction medium, if appropriate with the addition of a suitable auxiliary solvent.

The amount of acetic acid, water and, if appropriate, auxiliary solvent required depends on the solubility of the starting amine or its acetate. In the case of some amines having acetates which are readily soluble in water, such as, for example, 4-chloroaniline, a very dilute acetic acid is sufficient. In the case of other amines, for example 3,4-dichloroaniline, it is necessary to use an acetic acid of higher concentration. The amounts required can in each case be determined readily in simple preliminary tests. In every case at least 1 mole of acetic acid, in general 1–50 moles and preferably 1–20 moles, are employed for every amino group per mole of arylamine (I).

The auxiliary solvents concomitantly used can be water-soluble organic solvents. These include water-soluble alcohols and ethers, such as, for example, methanol, ethanol, propanol, isopropanol, glycol, diethylene glycol, triethylene glycol, glycol monomethyl ether, diethylene glycol monomethyl ether, tetrahydrofuran and dioxane; the following can also be used: solvents such as acetone, formic acid, dimethylformamide, N-methylpyrrolidone, tetramethylurea or sulpholane (tetramethylene sulphone).

Ethanol has proved particularly suitable as the auxiliary solvent; by its means it is possible to replace substantially the excess of acetic acid which is otherwise required as a solvent in many cases.

(It is also possible, when ethanol is used, to replace the remaining amount of acetic acid by benzoic acid; but no advantage can be seen in this). What is most preferable is either an excess of acetic acid as solvent or cheap alcohols, such as methanol and ethanol, as auxiliary solvents.

The auxiliary bases to be used are primarily alkali metal hydroxides, such as sodium hydroxide and potassium hydroxide, preferably in the form of their aqueous solutions. The alkali metal salts of weak acids, such as, for example, sodium carbonate, potassium bicarbonate and potassium acetate, can, however, also be employed.

The reaction temperature can be varied within a certain range; it should be so chosen that the reaction medium remains liquid and homogeneous, for example so that the acetic acid—in some cases dilute acetic acid—does not crystallize out. Hence the temperature range from $-20°$ C. to $+60°$ C. is suitable. It is preferable to carry out the reaction between 0° C. and 40° C., particularly advantageously between 5° and 25° C. (A slight amount of acetic acid which has crystallized out can, however, be desirable in some cases, since part of the heat of reaction can be removed by means of the heat of fusion). In general, the reaction is carried out under normal pressure.

If cyanogen chloride is added under these conditions to the homogeneous solution of the starting amine, the formation of the corresponding cyanamide sets in immediately. The pH of the solution falls and must be kept within a weakly acid range (pH$<$7 and $>$3) by adding auxiliary base (for example NaOH), since otherwise the reaction comes to a standstill or undesirable, interfering side reactions take place.

On the other hand, an alkaline medium must also be avoided, since in this case interfering side reactions would also take place, leading to impure products. It has proved particularly expedient and advantageous to ensure that a slight excess of cyanogen chloride relative to the amount of auxiliary base employed is always present during the reaction (pH$<$7).

In general, as indicated above, 1–2 moles of cyanogen chloride and 1–1.5 molar equivalents of an auxiliary base, preferably 1.01–1.5 moles of cyanogen chloride and 1.0–1.3 molar equivalents of an auxiliary base, and particularly preferentially 1.05–1.3 moles of cyanogen chloride and 1.0–1.15 molar equivalents of the auxiliary base are employed for each amino group per mole of arylamine (I) in carrying out the process; in this connection the molar ratio of cyanogen chloride to auxiliary base should be greater than 1 at any instant of the reaction.

The working up and isolation of the reaction products depends on the particular arylamine (I) employed and on the stoichiometry of reaction associated therewith.

In the simplest case, when the resulting cyanamide has been completely precipitated, it can be isolated by filtration with suction. If, on the other hand, it is necessary to maintain a homogeneous medium until the end of the reaction so that the amine is not co-precipitated and thereby escapes reaction, it is either possible to stir the reaction mixture into water or the bulk of the acetic acid is first carefully removed by distillation under reduced pressure and water is then added to the highly concentrated reaction mixture; by this means the salts (chlorides) of the auxiliary base are in each case brought into, or kept in, solution and the cyanamides which have been formed are precipitated and can then once more be isolated by filtration with suction.

Cyanamides of extremely weakly basic, primary arylamines (which sometimes are not immediately obtained in a very pure state) can be isolated most suitably by reprecipitation and subsequent filtration with suction. This method consists in treating the crude product initially formed with alkali metal hydroxide solution, small amounts of insoluble components are removed by filtration and the desired cyanamide is then reprecipitated by carefully acidifying the filtrate, which contains the alkali-soluble components.

The arylcyanamides (II) which can be prepared in accordance with the invention are solids. However, problems arise in characterizing them by determination of melting point owing to the thermal decomposition which takes place in most cases (see "Analysis" in the experimental section).

The aryl cyanamides which can be prepared in accordance with the invention can be used as intermediate products for the preparation of, for example, anti-inflammatory compounds (see Japanese Pat. No. A-55-141,472), of coccidiostatic agents (see U.S. Pat. No. 3,830,928), of sedatives, analgaesics and anaesthetics (see Belgian Pat. No. A-872,163) and of diuretics (see German Pat. No. A-2,251,354). The biscyanamides and triscyanamides of the general formula (II), in which n=2 or 3, are also valuable polymerizable monomers, since it is possible to prepare from them polymeric compounds which in some cases have highly developed film-forming properties (see German Pat. No. A-2,019,214).

The following examples serve to illustrate the invention further.

EXAMPLES

Some of the cyanamides prepared in accordance with the invention are new.

Note on Analysis

Since nearly all the melting points are decomposition points, the criterion of purity for the cyanamides obtained from primary arylamines was their complete solubility in dilute aqueous sodium hydroxide solution (10% strength NaOH) and purity as evidenced by a thin layer chromatogram by means of a double determination using different mixtures of mobile phases, employing the possible byproducts (that is to say amines and urea) as comparison substances.

All the arylcyanamides prepared in accordance with the invention proved to be pure substances; they were completely soluble—if derived from primary arylamines—in dilute sodium hydroxide solution, and no impurities could be detected in the thin layer chromatogram. All the cyanamides exhibit an intense, broad and in some cases split CN band in the IR spectrum (within the range: 2170–2230 cm$^{-1}$). The arylcyanamides can also be characterized by their molecular ions in their mass spectra (partially by means of coupled gas chromatography—mass spectroscopy).

Example 1

4-Chlorophenyl cyanamide (according to the invention):

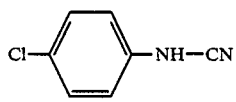

12.8 g (0.1 mole) of 4-chloroaniline were dissolved in 50 ml of glacial acetic acid, and 350 ml of water were added: 6.1 ml (0.12 mole) of cyanogen chloride were added at 10° C. to this homogeneous solution, and 110 ml of 1N NaOH were added dropwise in the course of 15 minutes with slight cooling. The mixture was stirred for a further 30 minutes and the product was filtered off with suction, washed and dried.

This gave 12.7 g of 4-chlorophenyl cyanamide (84% of theory) containing no impurities according to examination by thin layer Chromatography; the substance gave a clear solution in 2N NaOH.

Comparison Example 1a

4-Chlorophenyl cyanamide, analogously to: Synthesis 1976, page 592. (Cyanogen bromide was replaced by cyanogen chloride; weakly basic amine)

27.6 g (0.2 mole) of potassium carbonate were added to a solution containing 5.1 ml (0.1 mole) of cyanogen chloride in 100 ml of tetrahydrofuran, and a solution of 12.7 g (0.1 mole) of 4-chloroaniline in 100 ml of tetrahydrofuran was added dropwise at approximately −15° C. After a further 2 hours no reaction could be detected in a thin layer chromatogram. Only when the mixture was warmed to room temperature did a slightly exothermic reaction set in and the appearance of 4-chlorophenyl cyanamide could be detected by thin layer chromatography. When the reaction was complete, the mixture was concentrated. The residue was stirred with methylene chloride and sodium carbonate solution, and the aqueous alkaline phase was separated off and acidified. 2.5 g (16.5% of theory) of 4-chlorophenyl cyanamide were obtained.

Carrying out the reaction analogously with BrCN gave 5.3 g (35% of theory) of 4-chlorophenyl cyanamide.

Comparison Example 1b

4-Chlorophenyl cyanamide, analogously to: M. P. Pierron, Bull. Soc. Chim. 35, page 1203 (1906) (cyanogen chloride and 4-chloroaniline instead of cyanogen bromide and 4-bromoaniline)

4.2 ml (82.8 mmoles) of cyanogen chloride were added to 10 g (78.4 mmoles) of 4-chloroaniline, 200 ml of ethanol and a solution of 8.8 g (87.7 mmoles) of potassium bicarbonate in 40 ml of water, and the mixture was stirred at room temperature for 18 hours. It was then rendered alkaline by means of 11.06 g (80 mmoles) of potassium carbonate and was concentrated. 200 ml of water were added to the residue (pH 9-10), and the mixture was then filtered with suction and the alkaline solution was acidified. 3.1 g (26% of theory) of 4-chlorophenyl cyanamide (pure according to thin layer chromatography) were precipitated.

Comparison Example 1c

4-Chlorophenyl cyanamide, analogously to: Journal of the Indian Institute of Science, 29 A, page 3 (1946); ≅C. A. 41; 6214 h (the instructions are similar to those of Pierron)

7.2 ml (0.1415 mole) of cyanogen chloride were employed instead of cyanogen bromide. It was possible to isolate 1 g (46% of theory) of 4-chlorophenyl cyanamide.

Example 2

3,4-Dichlorophenyl cyanamide (according to the invention)

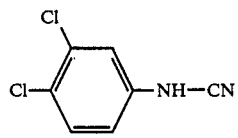

Variant a 163 g (1 mole) of 3,4-dichloroaniline were dissolved in 1,985 g of 90% strength acetic acid, and 61.2 ml (1.2 mole) of cyanogen chloride were then added at 10° C.

1100 ml of 1N NaOh were then run in at 5°-10° C., the mixture was then stirred for a further 2 hours and filtered with suction, and the residue was washed with water and dried.

144.5 g of 3,4-dichlorophenyl cyanamide were obtained. A further 27.4 g of product were precipitated by diluting the mother liquor with water. Both fractions gave a clear solution in approximately 2N NaOH and were homogeneous according to examination by thin layer chromatography. The total yield of pure 3,4-dichlorophenyl cyanamide was thus 171.9 g (92% of theory).

Variant b 16.2 g (0.1 mole) of 3,4-dichloroaniline were dissolved in 278 g of 64% strength acetic acid; 6.1 ml (0.12 mole) of cyanogen chloride were added at 10° C. and 22 g (0.11 mole) of 20% strength NaOH solution were then added dropwise slowly, with stirring. The mixture was stirred for a further 2 hours at room temperature and filtered with suction, and the filter residue was washed with water and dried. This gave 15 g (≃80% of theory) of 3,4-dichlorophenyl cyanamide which gave a clear solution in 2N NaOH and was homogeneous according to examination by thin layer chromatography.

A further 2 g (≃11% of theory) of pure 3,4-dichlorophenyl cyanamide were precipitated on diluting the mother liquor with water. The total yield was thus 26 g (≃91% of theory).

The above reaction was repeated, but using 200 ml of 90% strength acetic acid. When the reaction was complete, the mixture was concentrated and the residue was washed with water. Yield 16.8 g (≃90% of theory) of product which was homogeneous according to examination by thin layer chromatography.

Variant c 16.3 g (0.1 mole) of 3,4-dichloroaniline were dissolved in 200 ml of glacial acetic acid, 6.1 ml (0.12 mole) of cyanogen chloride were added at 14° C., and a solution of 7.6 g (0.055 mole) of potassium carbonate in 10 ml of water was added dropwise slowly, with cooling, at 10° C. The mixture was stirred for a further 2 hours at room temperature and was then concentrated under a water pump vacuum, the residue was stirred with 10% strength NaOH and filtered with suction and the solution was acidified.

This gave 15.1 g (≃81% of theory) of 3,4-dichlorophenyl cyanamide which was homogeneous according to examination by thin layer chromatography.

Variant d 16.3 g (0.1 mole) of 3,4-dichloroaniline were dissolved in 278 g of 64% strength acetic acid, and 6.1 ml (0.12 mole) Of cyanogen chloride were added at 10° C.; a total of 9.2 g (0.11 mole) of sodium bicarbonate was added slowly at a temperature below 10° C.

After 2 hours the mixture was filtered and the filter residue was washed with water and dried. 16.4 g (≃88% of theory) of 3,4-dichlorophenyl cyanamide were obtained. The substance was soluble in 2N NaOH and was homogeneous according to examination by thin layer chromatography.

Variant e 6.1 ml (0.12 mole) of cyanogen chloride were added, at a temperature below 10° C., to 16.3 g (0.1 mole) of 3,4-dichloroaniline in 150 ml of ethanol and 40 g of 50% strength acetic acid. 110 ml of 1N NaOH solution was then added dropwise. The mixture was stirred for a further hour and concentrated under a water pump vacuum until a bath temperature of 30° C. had been reached, and the residue was washed with water. 17.8 g (≃95% of theory) of 3,4-dichlorophenyl cyanamide were obtained. The substance was homogeneous according to examination by thin layer chromatography and gave a clear solution in 2N NaOH.

Comparison Example 2a

Analogously to: Tetrahedron 38, page 1771 (1982) (cyanogen bromide was replaced by cyanogen chloride; in addition, a weakly basic amine was employed)

163 g (1 mole) of 3,4-dichloroaniline and 61.2 ml (1.2 mole) of cyanogen chloride in 250 ml of 1M acetic acid/sodium acetate were stirred at room temperature for 4 hours. The mixture was then filtered with suction and the filter residue was washed with water and dried. 171.5 g of crude product were obtained. 81.1 g of this were digested with approximately 2N NaOH, and the insoluble residue was filtered off; the filtrate was acidified and the precipitate deposited was filtered off, washed with water and dried. This left as residue 40.4 g of 3,4-dichlorophenyl cyanamide which, according to examination by thin layer chromatography, still contained small amounts of two unknown impurities. The yield after purification was thus 45.4% of theory. According to examination by thin layer chromatography, the fraction insoluble in alkali consisted largely of unreacted 3,4-dichloroaniline.

Comparison Example 2b 0.2 mole of 3,4-dichloroaniline were reacted with 0.4 mole of cyanogen chloride analogously to the above instructions in 2a. Working up via sodium hydroxide solution gave 59% of theory of the desired product, which, according to examination by thin layer chromatography, still contained a small amount of an unknown impurity.

Example 3

3-Nitrophenyl cyanamide (according to the invention)

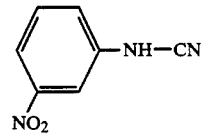

13.8 g (0.1 mole) of 3-nitroaniline were dissolved in 190 g of 79% strength acetic acid, and 6.1 ml (0.12 mole) of cyanogen chloride were added at 10° C.; 110 ml of 1N NaOH were added dropwise in the course of 3 hours. The mixture was then concentrated, digested with approximately 2N NaOH and filtered, the filtrate was acidified and the product precipitated was filtered off with suction, washed and dried.

This gave 13.1 g (80.4% of theory) of 3-nitrophenyl cyanamide which, according to examination by thin layer chromatography, was homogeneous.

Comparison Example 3

3-Nitrophenyl cyanamide analogously to: Tetrahedron 38, page 1771 (1982) (cyanogen bromide was replaced by cyanogen chloride; weakly basic amine)

13.8 g (0.1 mole) of 3-nitroaniline and 25.5 ml (0.5 mole) of cyanogen chloride in 250 ml of 1M acetic acid/sodium acetate were stirred at room temperature for 4 hours. The mixture was then filtered with suction, the precipitate was digested with approximately 2N NaOH, and the alkali-soluble fraction was reprecipitated by acidification. This gave 10.5 g (64% of theory) of 3-nitrophenyl cyanamide which, according to examination by thin layer chromatography, still contained a small amount of an impurity.

Example 4

1,4-Biscyanaminobenzene (according to the invention)

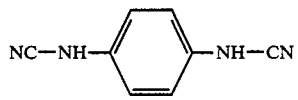

21.6 g (0.2 mole) of p-phenylenediamine were dissolved in 500 ml of 90% strength aqueous acetic acid, and 24.4 ml (0.48 mole) of cyanogen chloride were added at 15° C.; 440 ml of 1N NaOH were then added dropwise. The mixture was then filtered with suction and the filter residue was washed with water and dried. 28.6 g (90% of theory) of 1,4-biscyanaminobenzene were obtained. The substance was homogeneous according to examination by thin layer chromatography and gave a clear solution in 2.5N NaOH as well as in dilute ammonia.

Example 5

4,4'-Biscyanaminodiphenylmethane (according to the invention)

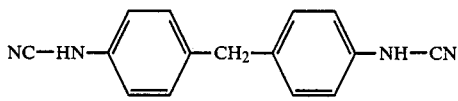

594 g (3 moles) of 4,4'-diaminodiphenylmethane were dissolved in 3 l of glacial acetic acid and 300 ml of water, and 366 ml (7.2 moles) of cyanogen chloride were added at 10°–15° C.; 2200 ml (6.6 moles) of 3N NaOH were then added slowly.

The precipitated solid was filtered off with suction and washed; a further fraction was precipitated from the mother liquor by dilution. All told, 696 g (93% of theory) of 4,4'-biscyanaminodiphenylmethane were obtained after drying in a vacuum cabinet. The substance was homogeneous according to examination by thin layer chromatography and gave a clear solution in dilute sodium hydroxide solution.

The following compound can also be prepared analogously to Example 5 (Example 6).

Example 6

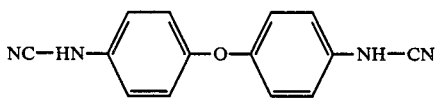

(Yield 84% of theory)

The compounds of the formula (II) listed in Table 1 below have also been prepared analogously to the foregoing examples, no optimization being carried out in respect of maximum yield:

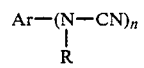

TABLE 1

| Example No. | Ar | R | n | Yield |
|---|---|---|---|---|
| 7 | phenyl | H | 1 | * |
| 8 | 3,5-dichlorophenyl | H | 1 | 81% |
| 9 | 2-chlorophenyl | H | 1 | 82% |
| 10 | 3-chlorophenyl | H | 1 | 80% |
| 11 | 3-trifluoromethylphenyl | H | 1 | 79% |
| 12 | 4-methyl-3-nitrophenyl | H | 1 | 85% |
| 13 | 2-methoxy-4-nitrophenyl | H | 1 | 91% |
| 14 | 4-methoxyphenyl | H | 1 | 70% |
| 15 | 2-acetamido-4-methylphenyl | H | 1 | 74% |
| 16 | 4-acetamidophenyl | H | 1 | 85% |

TABLE 1-continued

| Example No. | Ar | R | n | Yield |
|---|---|---|---|---|
| 17 | 4-Cl-2,5-di(OCH$_3$)-phenyl | H | 1 | 79% |
| 18 | 4-(CH$_3$OOC)-phenyl | H | 1 | 73% |
| 19 | 2-Cl-phenyl | C$_2$H$_5$ | 1 | 71% |
| 20 | dibenzofuran-yl | H | 1 | 95% |
| 21 | naphthyl | H | 1 | 75% |
| 22 | phenyl (1,3-position) | H | 2 | 90% |
| 23 | 4-CH$_3$-phenyl (1,3-position) | H | 2 | 98.5% |
| 24 | 4-(F$_3$CO)-phenyl | H | 1 | 96% |

It will be understood that the specification and examples are illustrative but not limitative of the present invention and that other embodiments within the spirit and scope of the invention will suggest themselves to those skilled in the art.

What is claimed:

1. A process for the preparation of an aryl cyanamide comprising reacting an arylamine of the formula $$\text{Ar}-(\text{NH})_n$$
$$\phantom{Ar-(NH)_n}|$$
$$\phantom{Ar-(NH)_n}R$$

in which
Ar is aryl,
R is hydrogen or alkyl, and
n is 1, 2 or 3.
(excepting 2-nitroaniline, 4-nitroaniline and arylamines having a nucleophilic character equal to or lower than 2-nitroaniline and 4-nitroaniline), with cyanogen chloride in 1-2 times the molar amount per mole of amino group of the arylamine initially in a homogeneous liquid phase, using as reaction medium a solvent selected from the group consisting of acetic acid, acetic acid diluted with water, acetic acid diluted with a water-miscible organic auxiliary solvent and acetic acid diluted with water and a water-miscible organic auxiliary solvent, the reaction being effected in the presence of 1-1.5 molar equivalents of an auxiliary base for each amino group of the arylamine, there being more cyanogen chloride than equivalents of auxiliary base present in the reaction mixture at any point in time of the reaction, the pH of the reaction mixture being maintained below 7.

2. A process according to claim 1, wherein the reaction is carried out at a temperature from −20° C. to +60° C.

3. A process according to claim 1, wherein the reaction is carried out at a temperature from 0° C. to 40° C.

4. A process according to claim 1, wherein the reaction is carried out at a temperature from 5° to 25° C.

5. A process according to claim 1, wherein at least 1 mole of acetic acid is employed for each mole of amino group of the arylamine.

6. A process according to claim 1, wherein 1.01-1.5 moles of cyanogen chloride and 1.0-1.3 molar equivalents of an auxiliary base are employed for each mole of amino group of the arylamine.

7. A process according to claim 1, wherein 1.05-1.3 moles of cyanogen chloride and 1.0-1.15 molar equivalents of an auxiliary base are employed for each mole of amino group of the arylamine.

8. A process according to claim 1, wherein ethanol is employed as an auxiliary solvent.

9. A process according to claim 1, wherein aqueous sodium hydroxide or potassium hydroxide solution is employed as the auxiliary base.

10. A process according to claim 1, wherein n is 1.

* * * * *

UNITED STATES PATENT AND TRADEMARK OFFICE
CERTIFICATE OF CORRECTION

PATENT NO. : 4,791,229
DATED : December 13, 1988
INVENTOR(S) : Rudolf Fauss, et al It is certified that error appears in the above-identified patent and that said Letters Patent is hereby corrected as shown below:

| | |
|---|---|
| Col. 1, lines 49-50 | Delete "thi-s" and substitute --this-- |
| Col. 2, line 49 | Delete "(j." and substitute --(J.-- |
| Col. 13, line 56 | At end of Table 1, insert --*) IR Spectrum: CN group; the product is alkali-soluble and decomposes on drying overnight; hence, the yield cannot be stated exactly.-- |

Signed and Sealed this

Seventeenth Day of October, 1989

Attest:

DONALD J. QUIGG

Attesting Officer     Commissioner of Patents and Trademarks